United States Patent
Li et al.

(10) Patent No.: US 9,846,116 B2
(45) Date of Patent: Dec. 19, 2017

(54) METHODS FOR DETERMINING AND/OR ADJUSTING REDOX-ACTIVE ELEMENT CONCENTRATIONS IN REDOX FLOW BATTERIES

(71) Applicant: UniEnergy Technologies, LLC, Mukilteo, WA (US)

(72) Inventors: Liyu Li, Richland, WA (US); Yueqi Liu, Mukilteo, WA (US); Chenxi Sun, Seattle, WA (US)

(73) Assignee: UNIENERGY TECHNOLOGIES, LLC, Mukilteo, WA (US)

( * ) Notice: Subject to any disclaimer, the term of this patent is extended or adjusted under 35 U.S.C. 154(b) by 355 days.

(21) Appl. No.: 14/257,739

(22) Filed: Apr. 21, 2014

(65) Prior Publication Data

US 2015/0303504 A1     Oct. 22, 2015

(51) Int. Cl.
| | |
|---|---|
| *H01M 8/18* | (2006.01) |
| *H01M 8/04* | (2016.01) |
| *G01N 21/3577* | (2014.01) |
| *H01M 8/0444* | (2016.01) |
| *H01M 8/04791* | (2016.01) |
| *G01N 21/359* | (2014.01) |

(52) U.S. Cl.
CPC .... *G01N 21/3577* (2013.01); *H01M 8/04447* (2013.01); *H01M 8/04455* (2013.01); *H01M 8/04798* (2013.01); *H01M 8/188* (2013.01); *G01N 21/359* (2013.01); *Y02E 60/528* (2013.01)

(58) Field of Classification Search
CPC ............ H01M 8/188; H01M 8/04447; H01M 8/04798; H01M 8/04455; G01N 21/3577

USPC .......................................... 429/409; 356/436
See application file for complete search history.

(56) References Cited

U.S. PATENT DOCUMENTS

| | | | | |
|---|---|---|---|---|
| 6,143,443 | A | * 11/2000 | Kazacos | ............... H01M 8/188 429/188 |
| 7,855,005 | B2 | 12/2010 | Sahu | |
| 2008/0193828 | A1* | 8/2008 | Sahu | ................... B60L 11/1822 429/63 |
| 2013/0095362 | A1* | 4/2013 | Keshavarz | ........... H01M 8/188 429/105 |

FOREIGN PATENT DOCUMENTS

| | | |
|---|---|---|
| CN | 1844892 A | 10/2006 |
| CN | 101657922 A | 2/2010 |
| CN | 101995385 A | 3/2011 |

(Continued)

OTHER PUBLICATIONS

Jinwei et al., Machine translation of CN 102621085 A, Aug. 2012.*

(Continued)

*Primary Examiner* — Sean P Cullen
(74) *Attorney, Agent, or Firm* — Christensen O'Connor Johnson Kindness PLLC

(57) ABSTRACT

Methods of determining concentrations and/or amounts of redox-active elements at each valence state in an electrolyte solution of a redox flow battery are provided. Once determined, the concentrations and/or amounts of the redox-active elements at each valence state can be used to determine side-reactions, make chemical adjustments, periodically monitor battery capacity, adjust performance, or to otherwise determine a baseline concentration of the redox-active ions for any purpose.

7 Claims, 6 Drawing Sheets

(56) References Cited

FOREIGN PATENT DOCUMENTS

| CN | 101995386 A | 3/2011 |
|---|---|---|
| CN | 102279218 A | 12/2011 |
| CN | 102539362 A | 7/2012 |
| CN | 102621085 A | 8/2012 |
| CN | 102866145 A | 1/2013 |

OTHER PUBLICATIONS

Chuanwei et al., Machine translation of CN 102539362 A, Jul. 2012.*
Chuanwei et al. Machine translation of CN 101995386 A, Mar. 2011.*
Gao, X., et al., "Spectroscopic Study of Vanadium Electrolytes," Department of Physics and Energy, Charles Parson Initiative on Energy and Sustainable Environment, University of Limerick, Ireland, presented at the 2013 IFBF (International Redox Flow Bettery Forum), Dublin, Ireland, Jun. 26-27, 2013.

* cited by examiner

METHODS FOR DETERMINING AND/OR ADJUSTING REDOX-ACTIVE ELEMENT CONCENTRATIONS IN REDOX FLOW BATTERIES

BACKGROUND

Concerns over the environmental consequences of burning fossil fuels and their resource constraints, along with the growing world demands in energy, have led to increasing penetration of renewable energy generated from sources such as solar and wind. However, the intermittent and varied nature of the renewable resources can make integration and dispatch of the renewable power challenging. Electrical energy storage (EES) can provide a solution to integration and dispatch of renewable power. Among the most promising EES technologies are redox flow batteries. A redox flow battery is an electrochemical device that is capable of storing up to megawatt-hours (MWhs) of electrical energy via a reversible electrochemical energy conversion.

In a redox flow battery, electrical energy is converted instantly to chemical potential (charge) or vice versa (discharge) at the electrodes as the negative and positive electrolyte solutions flow through the cell, and the electrical energy is stored as reduced and oxidized ionic species in the electrolyte solutions.

A redox flow battery has characteristics that render the battery suitable as an energy storage system: a redox flow battery can store and release electricity on demand; a redox flow battery can tolerate fluctuating power supplies and repetitive charge/discharge cycles at maximum rates; redox flow battery cycling can be initiated at any concentration of redox-active elements in the electrolytes; the power and energy of a redox flow battery can be separately designed, which can offer great flexibility to stationary applications; a redox flow battery potentially delivers a long cycle life; a redox flow battery can be safe, because the flowing electrolytes can carry away the heat generated from the electrode reactions and ohmic resistances; a redox flow battery can be charged at a rate that is as fast as or much faster than that of discharge; and a redox flow battery can store MWhs of electrical energy and can offer multi-MW power in a simple design and system setup.

The performance of a redox flow battery can be susceptible to decrease over time and/or usage. The concentration of each redox-active ion in the cathode electrolyte and the anode electrolyte and the respective volumes of the cathode electrolyte and anode electrolyte can provide an indication of battery performance, which can be monitored over time or at any state of battery life, for a given operating condition. The concentration of each redox-active ion in the cathode electrolyte and the anode electrolyte and the volumes of the cathode electrolyte and anode electrolyte can provide an indication of the energy in a redox flow battery that is available to meet application demands (e.g., peak shaving, wind power storage, voltage stabilization, etc.) presented by the connected load or end user. Therefore, there is a need to determine the concentrations of redox-active ions at any time during a redox flow battery's life cycle to determine side-reactions, make chemical adjustments, periodically monitor battery capacity, adjust performance, or to otherwise determine a baseline concentration of the redox-active ions for any purpose.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, this disclosure features a method of adjusting a concentration of a cathode redox-active element, a concentration of an anode redox-active element, or both the concentration of the cathode redox-active element and the concentration of the anode redox-active elements in a redox flow battery, including:

Step (1): providing a catholyte solution that includes a cathode redox-active element having one or more valence states; converting the cathode redox-active element at each valence state to a first predetermined valence state; and determining a concentration of the cathode redox-active element at each valence state;

Step (2): providing an anolyte solution that includes an anode redox-active element having one or more valence states; converting the anode redox-active element at each valence state to a second predetermined valence state; and determining a concentration of the anode redox-active element at each valence state; and Step (3): adjusting the concentration of the cathode redox-active element at each valence state in the catholyte solution, the concentration of the anode redox-active element at each valence state in the anolyte solution, or both the concentration of the cathode redox-active element at each valence state in the catholyte solution and the concentration of the anode redox-active element at each valence state in the anolyte solution, to meet a predetermined redox flow battery operating performance parameter.

In another aspect, this disclosure features a method of determining an amount of a redox-active element in a catholyte and an anolyte of a redox flow battery, including:

Step (1): providing an amount of a catholyte solution that includes a cathode redox-active element having one or more valence states; converting the cathode redox-active element at each valence state to a first predetermined valence state; and determining a concentration of the cathode redox-active element at each valence state;

Step (2): providing an amount of an anolyte solution that includes an anode redox-active element having one or more valence states; converting the anode redox-active element at each valence state to a second predetermined valence state; and determining a concentration of the anode redox-active element at each valence state; and Step (3): determining an amount of the cathode redox-active element at each valence state based on the concentration of the cathode redox-active element at each valence state and a volume of the catholyte solution, and determining an amount of the anode redox-active element at each valence state based on the concentration of the anode redox-active element at each valence state and a volume of the anode solution.

In yet another aspect, this disclosure features a method of determining a vanadium ion concentration in a vanadium redox flow battery, including: providing a catholyte solution that includes $V^{4+}$ and $V^{5+}$, converting the $V^{5+}$ to $V^{4+}$, and determining a concentration of each of $V^{5+}$ and $V^{4+}$ in the catholyte solution; and providing an anolyte solution than includes $V^{2+}$, $V^{3+}$, or both $V^{2+}$ and $V^{3+}$; converting each of the $V^{2+}$ and $V^{3+}$, when present, to $V^{4+}$; and determining the concentration of each of $V^{2+}$ and $V^{3+}$, when present, in the anolyte solution.

In yet another aspect, this disclosure features a method of determining a vanadium concentration in an electrolyte solution in a vanadium redox flow battery, including providing an electrolyte solution that includes $V^{3+}$ and $V^{4+}$; converting the $V^{3+}$ to $V^{4+}$; and determining the concentration of each of $V^{3+}$ and $V^{4+}$ in the electrolyte solution.

Embodiments of the methods of the disclosure can include one or more of the following features, in any combination.

In some embodiments, the predetermined redox flow battery operating performance parameter includes a baseline concentration and/or amount of the cathode redox active element at each valence state in the catholyte solution. Adjusting the concentration and/or amount of the cathode redox-active element can include comparing the concentration of the cathode redox-active element at each valence state in the catholyte solution to the baseline concentration and/or amount of the cathode redox active element at each valence state; and restoring the concentration and/or amount of the cathode redox-active element at each valence state in the catholyte solution to the baseline concentration and/or amount of the cathode redox-active element at each valence state. In some embodiments, adjusting the concentration and/or amount of the cathode redox-active element at each valence state includes adding an oxidant or a reductant, adding to or removing from the catholyte solution an amount of the cathode redox-active element, and/or adding an amount of the anolyte to the catholyte solution.

In some embodiments, the predetermined battery operating performance parameter includes a baseline concentration and/or amount of the anode redox active element at each valence state in the anolyte solution. Adjusting the concentration of the anode redox-active element can include comparing the concentration and/or amount of the anode redox-active element at each valence state in the anolyte solution to the baseline concentration of the anode redox active element at each valence state; and restoring the concentration and/or amount of the anode redox-active element at each valence state in the anolyte to the baseline concentration and/or amount of the anode redox-active element at each valence state. In some embodiments, adjusting the concentration and/or amount of the anode redox-active element at each valence state includes adding an oxidant or a reductant, adding to or removing from the anolyte solution an amount of the anode redox-active element, and/or adding an amount of catholyte to the anolyte solution.

In some embodiments, the first and second predetermined valence states are the same, such as when the cathode redox-active element and the anode redox-active element are the same.

In some embodiments, converting the cathode redox-active element includes reducing the cathode redox-active element to the first predetermined valence state. In some embodiments, reducing the cathode redox-active element includes exposing the cathode redox-active element to a reducing agent selected from the group consisting of $Sn^{2+}$, $Fe^{2+}$, sulfites, phosphites, hypophosphites, phosphorous acid, metal hydrides, metals, metal amalgams, and diboranes. In some embodiments, reducing the cathode redox-active element includes exposing the cathode redox-active element to a reducing agent selected from the group consisting of sugars, alcohols, organic acids, oils, and hydrocarbons. In some embodiments, the reducing agent is a sulfite.

In some embodiments, converting the anode redox-active element includes oxidizing the anode redox-active element to the second predetermined valence state.

In some embodiments, the methods are automated or semi-automated (e.g., using a computer-controlled system). The methods can be performed within a housing for a redox flow battery, or externally to a housing for a redox flow battery (e.g., in a field deployment).

In some embodiments, the cathode redox-active element and the anode redox-active element include vanadium and each of the first and second predetermined valence states can be $V^{4+}$. Oxidizing the anode redox-active vanadium can include exposing the anode redox-active element to an oxidizing agent including a solution of known concentrations of $V^{4+}$ and $V^{5+}$. In some embodiments, determining an amount of $V^{4+}$ and $V^{5+}$ is based on the concentration of each of $V^{4+}$ and $V^{5+}$ and a volume of the catholyte solution, and determining an amount $V^{2+}$, $V^{3+}$, or both $V^{2+}$ and $V^{3+}$ is based on the concentration of each of $V^{2+}$, $V^{3+}$, when present, and a volume of the anolyte solution. In some embodiments, determining an amount of $V^{3+}$ and $V^{4+}$ is based on the concentration of each of $V^{3+}$ and $V^{4+}$ and a volume of the electrolyte solution. The method can further include determining a $V^{4+}$ optical absorption spectroscopy calibration curve from $V^{4+}$ standard solutions.

In some embodiments, converting the $V^{5+}$ to $V^{4+}$ includes exposing the $V^{5+}$ to a reducing agent selected from the group consisting of $Sn^{2+}$, $Fe^{2+}$, sulfites, phosphites, hypophosphites, phosphorous acid, metal hydrides, metals, metal amalgams, and diboranes. In some embodiments, converting the $V^{5+}$ to $V^{4+}$ includes exposing the $V^{5+}$ to a reducing agent selected from the group consisting of sugars, alcohols, organic acids, oils, and hydrocarbons. In some embodiments, converting each of the $V^{2+}$ and $V^{3+}$, when present, to $V^{4+}$ includes oxidizing exposing each of the $V^{2+}$ and $V^{3+}$ to a solution containing known concentrations of $V^{5+}$ and $V^{4+}$. In some embodiments, converting the $V^{3+}$ to $V^{4+}$ includes exposing the $V^{3+}$ to an oxidizing agent comprising a solution containing known concentrations of $V^{5+}$ and $V^{4+}$.

In some embodiments, when the electrolyte solution includes $V^{3+}$ and $V^{4+}$, the electrolyte solution can be a mixed solution of a catholyte and an anolyte in a vanadium redox flow battery. For example, the electrolyte solution can be an initial electrolyte in a vanadium redox flow battery.

In some embodiments, determining the concentration of the redox-active element (e.g., cathode redox active element, anode redox-active element, etc.) includes using optical absorption spectroscopy.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

The present disclosure is generally directed to methods for determining a concentration of a given redox-active element at a given valence state in a redox flow battery. Once known, the concentration of the given redox-active element at a given valence state, together with a volume of an electrolyte that includes the given redox-active element, can allow for adjustments of a redox flow battery's performance. Adjustment of a redox flow battery's performance can be carried out, for example, to improve battery efficiency, energy utilization, and/or to provide information to supervisory and/or control systems. A known concentration of a given redox-active element at a given valence state can provide a basis for adjusting the concentration and/or amount of redox-active elements at various valence states in an electrolyte solution to meet a predetermined redox flow battery operating performance parameter, such as a baseline concentration and/or amount of the redox-active elements at each valence state.

Redox Flow Battery

Figure 1:
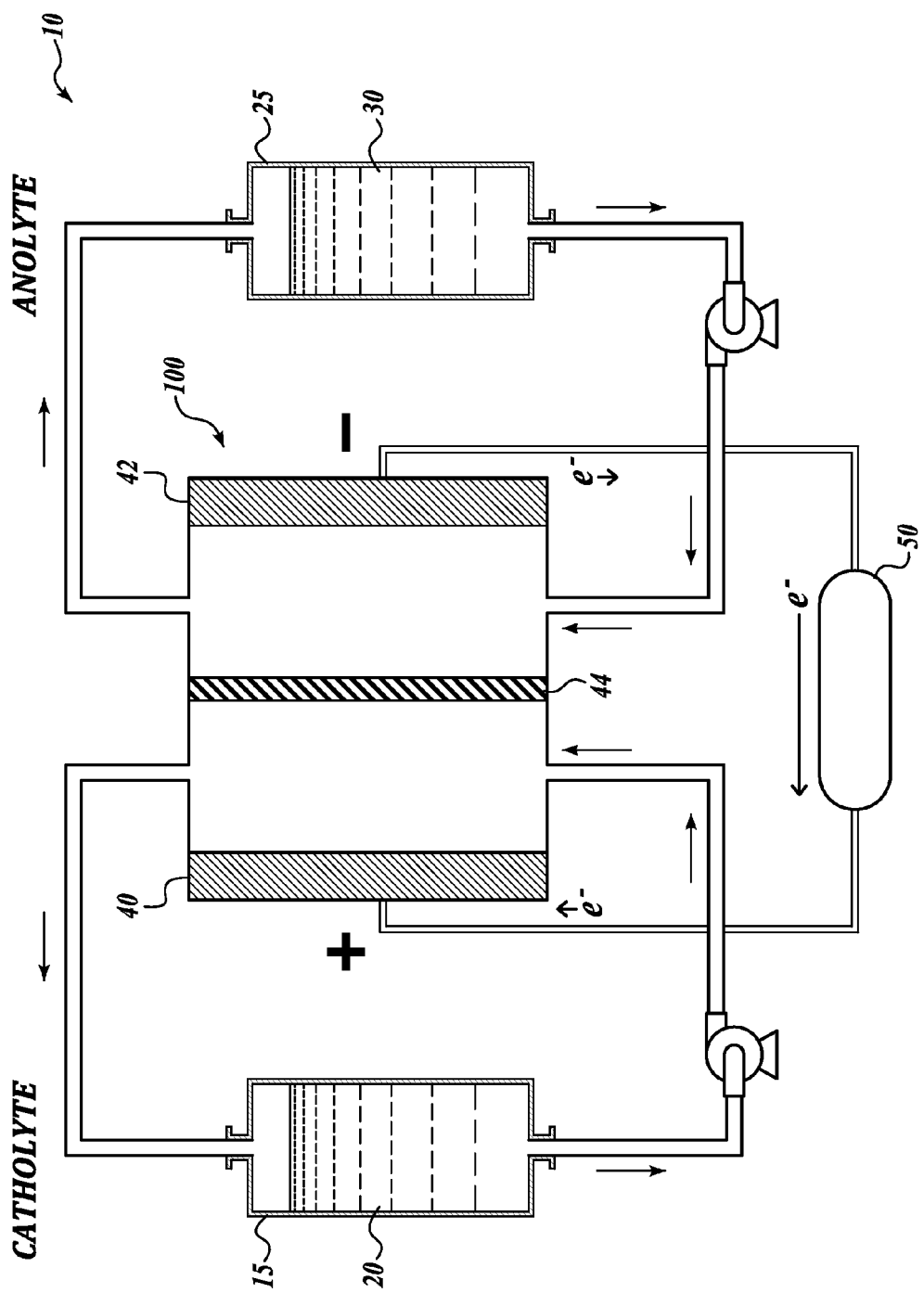
FIG. 1 is a schematic representation of a redox flow battery.

A schematic illustration of a representative redox flow battery is shown in FIG. 1. Referring to FIG. 1, a redox flow battery 10 includes an electrochemical cell 100 that includes a positive electrode 40, a negative electrode 42, and a membrane or separator 44 between positive electrode 40 and negative electrode 42 that allows for selective conduction of ionic charges for charge transportation and compensation. The redox flow battery also includes a catholyte (i.e., positive electrolyte) 20 contained in catholyte tank 15, and an anolyte (i.e., negative electrolyte) 30 contained in anolyte tank 25. Catholyte 20 includes cathode redox-active ions and anolyte 30 includes anode redox-active ions.

While a single electrochemical cell 100 is illustrated in FIG. 1, it will be appreciated that multiple electrochemical cells, assembled into a stack, can also be used in a redox flow battery.

During operation, catholyte 20 and anolyte 30 are delivered to electrochemical cell 100 from storage tanks 15 and 25, respectively. During battery charge, a power element 50 operates as a power source, providing electrical energy that is stored as chemical potential in the catholyte 20 and anolyte 30. Thus, anode redox-active ions are reduced on the negative electrode 42, while cathode redox-active ions are oxidized on the positive electrode 40. The power source can be any power source known to generate electrical power, including, but not limited to, renewable power sources, such as wind, solar, and hydroelectric. Traditional power sources, such as combustion, can also be used.

During battery discharge, redox flow battery 10 is operated to transform the chemical potential stored in the catholyte 20 and anolyte 30 into electrical energy that is then discharged at the power element 50, which acts as an electrical load. FIG. 1 illustrates the flow of electrons ("$e^-$") through the redox flow battery 10 in discharge mode, where the electrochemical reactions of redox flow battery 10 are essentially the opposite of the electrochemical reactions during battery charge.

Figure 2:
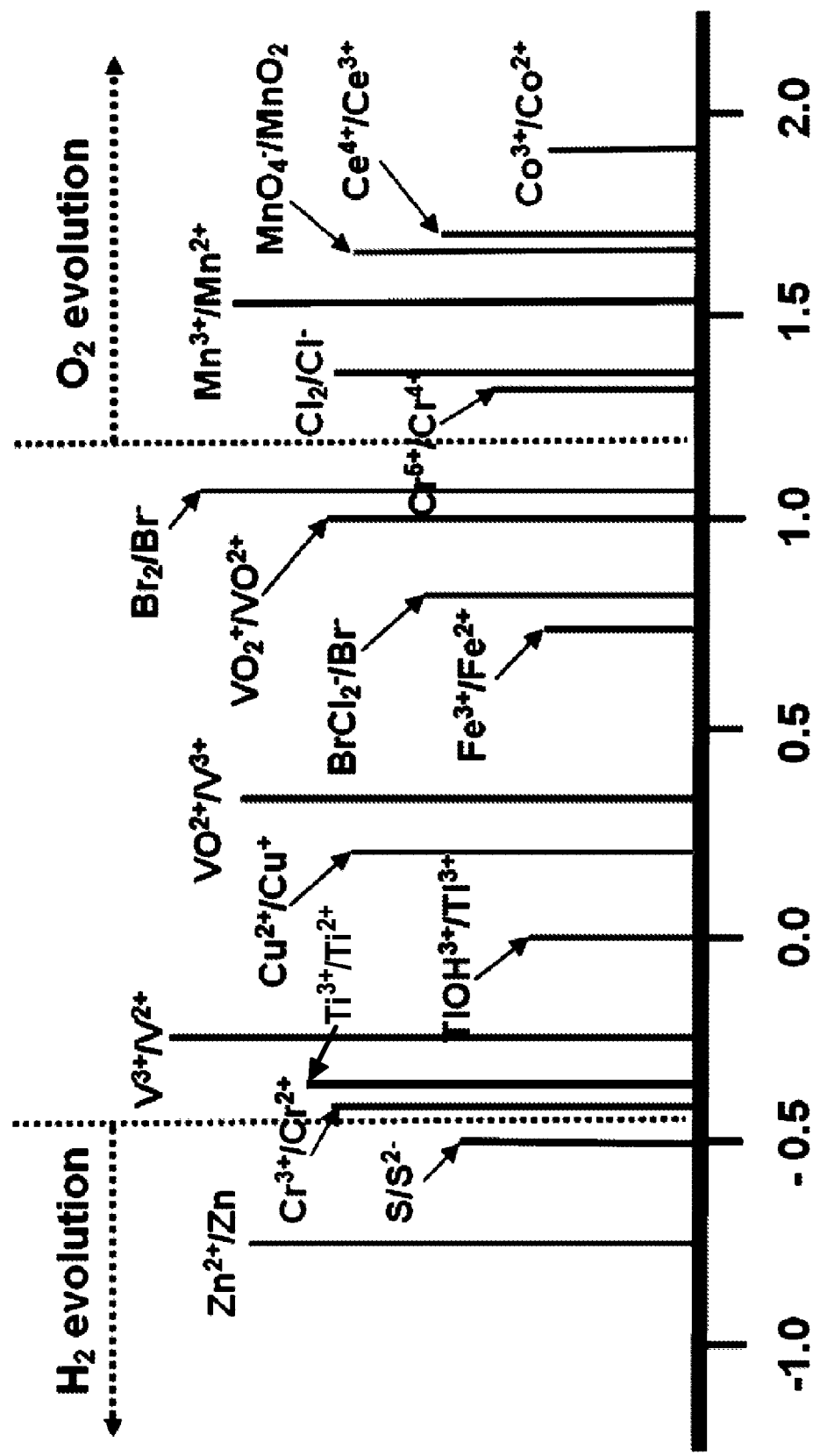
FIG. 2 is a diagram showing embodiments of non-limiting examples of redox couples for a redox flow battery.

As discussed above, redox flow batteries include redox-active elements. Examples of redox-active elements include V, Br, S, Zn, Ce, Fe, Mn, and Ti. FIG. 2 shows some exemplary metal redox couples and their standard potentials in an aqueous system. Non-limiting examples of redox couples can include $V^{2+}/V^{3+}$ vs. $V^{4+}/V^{5+}$, $V^{2+}/V^{3+}$ vs. $Br^-/ClBr_2$, $Br_2/Br^-$ vs. $S/S^{2-}$, $Br^-/Br_2$ vs. $Zn^{2+}/Zn$, $Ce^{4+}/Ce^{3+}$ vs. $V^{2+}/V^{3+}$, $Fe^{3+}/Fe^{2+}$ vs. $Br_2/Br^-$, $Mn^{2+}/Mn^{3+}$ vs. $Br_2/Br^-$, and $Fe^{3+}/Fe^{2+}$ vs. $Ti^{2+}/Ti^{3+}$.

During operation, a redox flow battery can have certain characteristics that can cause operating inefficiencies. For example, at an initial state, the charge capacity of each of the anolyte and catholyte reservoirs can initially be identical. However, as the battery is operated over extended periods of time under certain conditions, side reactions (e.g., oxidation, reduction, precipitation, and/or decomposition) can occur to cause a chemical imbalance between the anolyte and catholyte solutions, causing asymmetric capacity loss between the anolyte and the catholyte. This chemical imbalance can be corrected to adjust performance of the battery.

As a non-limiting example, in a vanadium flow redox battery prior to charging, the initial anolyte solution and catholyte solution each include identical concentrations of $V^{3+}$ and $V^{4+}$. Upon charge, the vanadium ions in the anolyte solution are reduced to $V^{2+}/V^{3+}$ while the vanadium ions in the catholyte solution are oxidized to $V^{4+}/V^{5+}$.

Over time, side reactions can occur in the vanadium battery as the anolyte is susceptible to $V^{2+}$ oxidation by atmospheric oxygen (thereby decreasing the amount and/or concentration of $V^{2+}$), $V^{2+}$ can also be oxidized by $H^+$ if hydrogen is evolved at the anode (thereby decreasing the amount and/or concentration of $V^{2+}$). Furthermore, precipitation of $V^{5+}$ as $V_2O_5$ can occur in the catholyte (thereby decreasing the amount and/or the concentration and amount of $V^{5+}$). Because of these side reactions, the vanadium flow redox battery can lose capacity as its catholyte and anolyte become chemically imbalanced. The reduced capacity of one of the electrolyte tanks can limit battery performance. The chemical imbalance can be corrected to increase battery efficiency.

Expressed mathematically, for a vanadium redox flow battery with the same quantities of electrochemically available vanadium ions at the anolyte and the catholyte (i.e., a chemically balanced vanadium redox flow battery), the concentrations of the redox-active vanadium ions in the anolyte and the catholyte can be represented by:

$$[V^{2+}]/([V^{2+}]+[V^{3+}]) \text{ at anolyte} = [VO_2^+]/([VO^{2+}]+[VO_2^+]) \text{ at catholyte}.$$

However, if the vanadium redox flow battery is chemically imbalanced, then:

$$[V^{2+}]/([V^{2+}]+[V^{3+}]) \text{ at anolyte} \neq [VO_2^+]/([VO^{2+}]+[VO_2^+]) \text{ at catholyte}.$$

While restoration of a chemically imbalanced redox flow battery to a chemically balanced redox flow battery is described above, in some embodiments, a redox flow battery can desirably be chemically imbalanced. The chemical imbalance can be predetermined and can be desirable, for example, to compensate for or to minimize possible side-reactions in a redox flow battery, and/or to reduce or prevent the likelihood of active species transfer across the separator. Correction of the chemical imbalance in this embodiment restores the amounts and/or the concentrations of the redox-active elements at various valence states to the desired predetermined imbalanced amounts and/or concentrations.

Thus, the efficiency of operation for a redox flow battery can be monitored by providing the concentrations and/or amounts of redox-active elements at various valence states in the electrolytes. The concentrations and/or amounts of redox-active elements at various valence states can provide a basis for adjusting concentrations of the redox-active elements at various valence states to achieve a predetermined battery operating parameter, which can include a battery at a chemically balanced state or a battery at a desired predetermined chemically imbalanced state. In some embodiments, the concentrations and/or amounts of redox-active elements at various valence states are used by battery operating algorithms, for example, to start or stop charge/discharge, to determine allowable charge/discharge rates, and/or to determine how much charge is left to support a particular application.

Existing methods used to determine the concentrations and/or amounts of redox-active elements at various valence states in the electrolytes are often time-consuming, inconsistent, inaccurate, or require the use of a laboratory. Thus, a method of analysis that can reliably, consistently, accurately, and rapidly determine the concentrations of redox-active elements at various valence states in a redox flow battery is needed. Such a method can be amenable to field-deployment using standardized chemicals and equipment.

Methods are provided herein for determining the concentrations and/or amounts of redox-active elements at various valence states in a redox flow battery, and using the concentrations and/or amounts of redox-active elements at various valence states to adjust battery performance by, for example, adjusting the concentrations and/or amounts of redox-active elements in various valence states to meet a battery operating performance parameter. The determination methods for the concentrations and/or amounts of redox-active elements at various valence states are rapid, reliable, consistent, accurate, and can be easily implemented using available analytical methods. The determination methods can be implemented in an automated or semi-automated manner (e.g., with a computer-controlled system) and the analytical methods can be externally to a housing for the redox flow battery, or internally within a housing for the redox flow battery.

Redox-Active Element Concentration and Amount Determinations

Methods to determine concentrations and/or amounts of redox-active elements at each valence state in a redox flow battery are provided. In general, the methods include (1) providing (e.g., withdrawing) a given electrolyte sample (e.g., a catholyte sample, an anolyte sample, an electrolyte sample prior to an initial charging process, or an electrolyte sample that is a mixture of a catholyte and an anolyte); (2) converting a redox-active element having one or more valence states in the sample to a single predetermined valence state, using an oxidizing agent and/or a reducing agent; (3) determining the concentration of the redox-active element at the single predetermined valence state in the original sample and after conversion; and (4) determining the concentration of the redox-active element at each valence state in the sample from the concentration of the converted single valence state redox-active element. The concentration of the redox-active element can be determined by mathematical calculation from the total concentration of the redox-active element in the sample (which can be determined by obtaining the concentration of the redox-active element at the single valence state, once all the redox-active element having one or more valence states have been converted), the concentration of oxidizing and/or reducing agent used to convert the redox-active element to a single valence state, and the concentration of any redox-active active element at the single predetermined valence state in the original sample. The amount of the redox-active elements at each valence state can then be determined based on the concentration of the redox-active elements at each valence state and the volume of the given electrolyte solution (e.g., by multiplying the concentration and the volume).

For example, to determine the concentrations of redox-active elements at various valence states in a catholyte of a redox flow battery, an amount of a catholyte solution including a cathode redox-active element at one or more valence states is withdrawn from a redox flow battery; the cathode redox-active element at each valence state is converted to a first predetermined valence state; and a concentration of the cathode redox-active element at each valence state is determined based on the concentration of the converted cathode redox-active element at the first predetermined valence state. The amount of redox-active elements at various valence states in the catholyte is then determined, based on the concentration of the cathode redox-active element at each valence state and the volume of the catholyte solution (e.g., by multiplying the concentration and the volume).

Similarly, to determine the concentrations of redox-active elements at various valence states in an anolyte of a redox flow battery, an amount of an anolyte solution including an anode redox-active element having one or more valence states is withdrawn from a redox flow battery, the anode redox-active element at each valence state is converted to a second predetermined valence state; and a concentration of the anode redox-active element at each valence state is determined based on the concentration of the converted anode redox-active element at the second predetermined valence state. The amount of redox-active elements at various valence states of the anolyte is then determined, based on the concentration of the anode redox-active element at each valence state and the volume of the anolyte solution (e.g., by multiplying the concentration and the volume).

In some embodiments, a baseline concentration of a redox-active element (e.g., a cathode redox-active element, an anode redox-active element, or a redox-active element in an electrolyte solution prior to an initial charging process) at each valence state is determined for comparison with a measured concentration of redox-active elements at various valence states of a battery (e.g., during operation or maintenance). The baseline concentration of the redox-active element can be determined by (1) providing a catholyte or anolyte solution after an initial charge of a redox flow battery, or providing an electrolyte solution prior to an initial charging process; (2) converting the redox active element at each valence state in each electrolyte solution to a predetermined valence state; (3) determining the concentration of the redox-active element at the single predetermined valence state in the original electrolyte solution and after conversion; (4) and determining the concentration of the redox-active element in the electrolyte solution at each valence state, as described above. The based amount of the redox-active elements at each valence state can then be determined based on the base concentration of the redox-active elements at each valence state and the volume of the given electrolyte solution (e.g., by multiplying the concentration and the volume).

In some embodiments, withdrawing an amount of catholyte and/or anolyte includes taking an amount of the catholyte or anolyte prior to or after electrolyte flow into the cathode or the anode, respectively, or directly from the catholyte or anolyte tanks. The withdrawal can occur periodically during battery maintenance, or at any time during battery operation. In some embodiments, withdrawing an amount of an initial electrolyte includes taking an amount of electrolyte from either of the anolyte or catholyte tank, prior to initial charging of the battery. In some embodiments, withdrawing an amount of a mixed electrolyte solution includes taking a sample from the catholyte tank, a sample from the anolyte tank, mixing the two samples, and allowing the redox-active element at various valence states to equilibrate. Withdrawing an amount of a mixed electrolyte solution can occur after discharge of a redox flow battery. The amount of the given electrolyte (e.g., the catholyte, the anolyte, an initial electrolyte solution, or a mixed electrolyte solution) that is withdrawn can be relatively little, for example, about 10 mL, 20 mL, or 30 mL.

The predetermined valence state can be a valence state that can afford a detectable signal with minimal background noise or interference from other chemical species in the electrolyte, using a given analytical method. When the cathode redox-active element and the anode redox-active element are the same, the predetermined valence states to which the cathode and/or anode redox-active element at each valence state are converted to can be the same.

In some embodiments, converting a cathode redox-active element having one or more valence states to a predetermined valence state includes exposing a cathode redox-active element to a reducing agent. The concentration of the reducing agent can be predetermined. Non-limiting examples of reducing agents include $Sn^{2+}$, $Fe^{2+}$, sulfites, phosphites, hypophosphites, phosphorous acid, metal hydrides, metals, metal amalgams, diboranes, sugars, alcohols, organic acids, oils, and/or hydrocarbons. In some embodiments, the reducing agent is sulfite. In some embodiments, the reducing agent can be a redox-active species that can form an electrochemical pair with the cathode redox-active element to be reduced and that has a lower standard potential than the cathode redox-active element to be reduced. For example, the reducing agent can be the same redox-active element at a lower valence state than the valence state of cathode redox-active element to be reduced, such as an anolyte solution of the redox flow battery being tested.

In some embodiments, converting an anode redox-active element having one or more valence states to a predetermined valence state includes oxidizing an anode redox-active element with an oxidizing agent. The concentration of the oxidizing agent can be predetermined. Non-limiting examples of oxidizing agents include oxygen, air, ozone, hydrogen peroxide, and permanganates. In some embodiments, the oxidizing agent can be a redox-active species that can form an electrochemical pair with the anode redox-active element to be reduced and that has a higher standard potential than the anode redox-active element to be reduced. For example, the oxidizing agent can be the same redox-active element at a higher valence state than the valence state of the anode redox-active element to be oxidized, such as a catholyte solution of the redox flow battery being tested.

The electrolyte solution (e.g., a catholyte, anolyte, or a mixed electrolyte solution) can be subjected to an analytical method, which can provide measurement of a detectable signal that can be correlated to the concentration of a given redox-active element at the predetermined valence state in the electrolyte solution. In some embodiments, determining the concentration of a given redox-active element (e.g., a cathode redox-active element, or an anode redox-active element) further includes determining a standard concentration calibration curve for the given redox-active element, at the same predetermined valence state to which the given redox-active element at each valence state is converted, at defined concentrations, using the analytical method. Determining the concentration of a given redox-active element can include matching a magnitude of a detectable signal in the electrolyte solution to a standard concentration calibration curve at the same magnitude of the detectable signal to determine the corresponding concentration.

Redox-Active Element Concentration and/or Amount Adjustment

After the concentrations and/or amounts of redox-active elements at various valence states are determined, (1) the concentration and/or amount of the cathode redox-active element at each valence state in the catholyte solution can be adjusted, (2) the concentration and/or amount of the anode redox-active element at each valence state in the anolyte solution can be adjusted, or (3) the concentration and/or amount of an initial or mixed electrolyte solution can be adjusted, to meet a predetermined redox flow battery operating performance parameter.

Representative predetermined redox flow battery operating performance parameters include, for example, energy capacity, power capacity, and power ramping rates. In some embodiments, the predetermined redox flow battery operating performance parameter includes a baseline concentration and/or amount of the cathode redox active element at each valence state in the catholyte solution, a baseline concentration and/or amount of the anode redox active element at each valence state in the anolyte solution, or a baseline concentration and/or amount of the redox-active element at each valence state in an electrolyte solution prior to an initial charging process. Upon determining the concentration and/or amount of the cathode redox-active element at each valence state, the concentration and/or amount of the cathode redox-active element at each valence state in the catholyte solution is compared to the baseline concentration and/or amount of the cathode redox active element at each valence state; and the concentration and/or amount of the cathode redox-active element at each valence state in the catholyte solution is restored to the baseline concentration and/or amount of the cathode redox-active element at each valence state. Similarly, upon determining the concentration and/or amount of the anode redox-active element at each valence state, the concentration and/or amount of the anode redox-active element at each valence state in the anolyte solution is compared to the baseline concentration and/or amount of the anode redox active element at each valence state; and the concentration and/or amount of the anode redox-active element at each valence state in the anolyte solution is restored to the baseline concentration and/or amount of the anode redox-active element at each valence state. A similar adjustment process can be carried out for redox-active elements at each valence state in an electrolyte solution prior to an initial charging process or in a mixed electrolyte solution, by comparing and restoring the concentration and/or amount of said electrolyte solution to a baseline concentration and/or amount of a reference electrolyte solution, prior to an initial charge.

To adjust the concentration and/or amount of the redox active element in a given electrolyte solution (e.g., a catholyte, an anolyte, an initial electrolyte solution, or a mixed electrolyte solution), an oxidizing agent or a reducing agent can be added to the given electrolyte solution to meet a predetermined redox flow battery operating performance parameter. In some embodiments, an amount of solvent (e.g., water, acid) can be added to adjust the concentration of the redox-active element. In some embodiments, adjusting the amount of redox-active element in a given electrolyte solution includes adding or removing a quantity of the given electrolyte solution.

Non-limiting examples of reducing agents and oxidizing agents for adjusting the concentration of a given electrolyte are as provided above.

Analytical Method

As noted above, an analytical method is used to measure of a detectable signal in a given electrolyte solution. The nature of analytical method is not critical so long as the method can accurately determine the concentration of a redox-active element to be analyzed. In some embodiments, the analytical method is optical absorption spectroscopy, such that absorbance of a given sample can be measured and correlated to the concentration of a redox-active element at a predetermined valence state. Optical absorption spectroscopy can be beneficial as it can be portable, easily implemented, and simple to operate. In some embodiments, the analytical method is a conventional method for directly detecting redox-active ions, such as potentiometric titration, inductively coupled plasma atomic emission spectrometry, or ion chromatography.

Vanadium Redox Flow Battery

In some embodiments, the redox flow battery is a vanadium flow redox flow battery, where the anolyte includes a mixture of $V^{2+}$ and $V^{3+}$, and the catholyte includes a mixture of $V^{4+}$ and $V^{5+}$. Thus, the redox-active element in both the anolyte and the catholyte is vanadium. When determining the concentration of vanadium at each valence state in the vanadium flow redox battery, the predetermined valence state to which the cathode redox-active ions are reduced and to which the anode redox-active ions are oxidized can be $V^{4+}$. In some embodiments, before determining the concentration of the cathode redox-active element and the anode redox-active element, a standard concentration calibration curve of a detectable signal vs. the concentration of $V^{4+}$ in a standard $V^{4+}$ solution is determined, for example, using optical absorption spectroscopy.

Oxidizing the anode redox-active element includes exposing the anode redox-active element vanadium at valence states 2+ and 3+ to an oxidizing agent, such as a solution of known concentrations of $V^{4+}$ and $V^{5+}$, to generate a solution of $V^{4+}$. Reducing the cathode redox-active element vanadium at a valence state of 5+ can include exposing the cathode redox-active element to a reducing agent, such as $Sn^{2+}$, $Fe^{2+}$, sulfites, phosphites, hypophosphites, phosphorous acid, metal hydrides, metals, metal amalgams, diboranes, sugars, alcohols, organic acids, oils, and/or hydrocarbons, to generate a solution of $V^{4+}$. In some embodiments, the reducing agent is sulfites, which exhibits minimal background signal when subjected to an analytical method, such as optical absorption spectroscopy.

Once the vanadium at each valence state is converted to $V^{4+}$, the concentration of $V^{4+}$ and $V^{5+}$ in the catholyte solution and the concentration of the $V^{2+}$ and $V^{3+}$ in the anolyte solution can be calculated from the amount of reducing agent and oxidizing agent used, respectively, the total concentration of vanadium in each electrolyte solution, and the concentration of $V^{4+}$ in each solution (which can be determined by comparing a detectable signal for $V^{4+}$ vs. the standard concentration calibration curve). Knowing the concentration of vanadium at each valence state and volume of each of the catholyte and anolyte solutions, the amount of vanadium at each valence state in the redox flow battery can be calculated.

In some embodiments, instead of a catholyte solution including $V^{4+}$ and $V^{5+}$ or an anolyte solution including $V^{2+}$ and $V^{3+}$, the electrolyte solution includes $V^{3+}$ and $V^{4+}$. The electrolyte solution can be an initial electrolyte solution that is loaded into a vanadium redox flow battery prior to any charging process. In some embodiments, the electrolyte solution is an electrolyte solution post-battery discharge, once the anolyte and the catholyte solutions have been mixed and allowed to equilibrate for a period of time.

To determine the concentrations of $V^{3+}$ and $V^{4+}$ in the electrolyte solution, $V^{3+}$ is converted to $V^{4+}$ by exposure to an oxidizing agent, such as a solution containing known concentrations of $V^{5+}$ and $V^{4+}$. The total $V^{4+}$ concentration of the solution can be determined by comparing a detectable signal against the standard concentration calibration curve for $V^{4+}$, and the concentration of each of $V^{3+}$ and $V^{4+}$ in the initial $V^{3+}/V^{4+}$ solution can be calculated from the total vanadium concentration and the known amount of $V^{5+}$ used to oxidize $V^{3+}$. Knowing the concentration of $V^{3+}$ and $V^{4+}$ and volume of the electrolyte solution, the amount of vanadium at each valence state in the electrolyte solution can be calculated.

The analytical method can be optical absorption spectroscopy and the detectable signal can be an absorbance at a predetermined wavelength. The predetermined wavelength can be one at which $V^{4+}$ absorbs while being substantially free of interfering absorbance values.

While the above describes methods for determining concentrations and amounts of redox-active vanadium ions for a vanadium redox flow battery, it is understood that the methods can be generalized for mixed redox-active element redox flow batteries.

Evaluation of sulfite as a non-interfering reducing agent is described in Example 1. Determination of suitable concentrations for measuring $VO^{2+}$ absorbance is described in Example 2. A protocol for standard concentration calibration curve for $VO^{2+}$ is described in Example 3. Protocols and mathematical calculations for determining concentrations of electrolyte solutions in an exemplary vanadium flow battery are described in Examples 4-7.

The following examples are provided for the purpose of illustrating, not limiting, the invention.

Example 1

Sodium Sulfite as a Reducing Agent for Vanadium Ion Analysis

The suitability of sodium sulfite (0.5 mol/L) as a reducing agent for analysis of vanadium ion concentration was investigated. The reducing agent should meet the requirement of no signal interference with $VO^{2+}$ ions analysis. Here, no absorption at the wavelength of 765 nm was observed in an optical absorption spectrum of the aqueous sodium sulfite solution.

Figure 3:
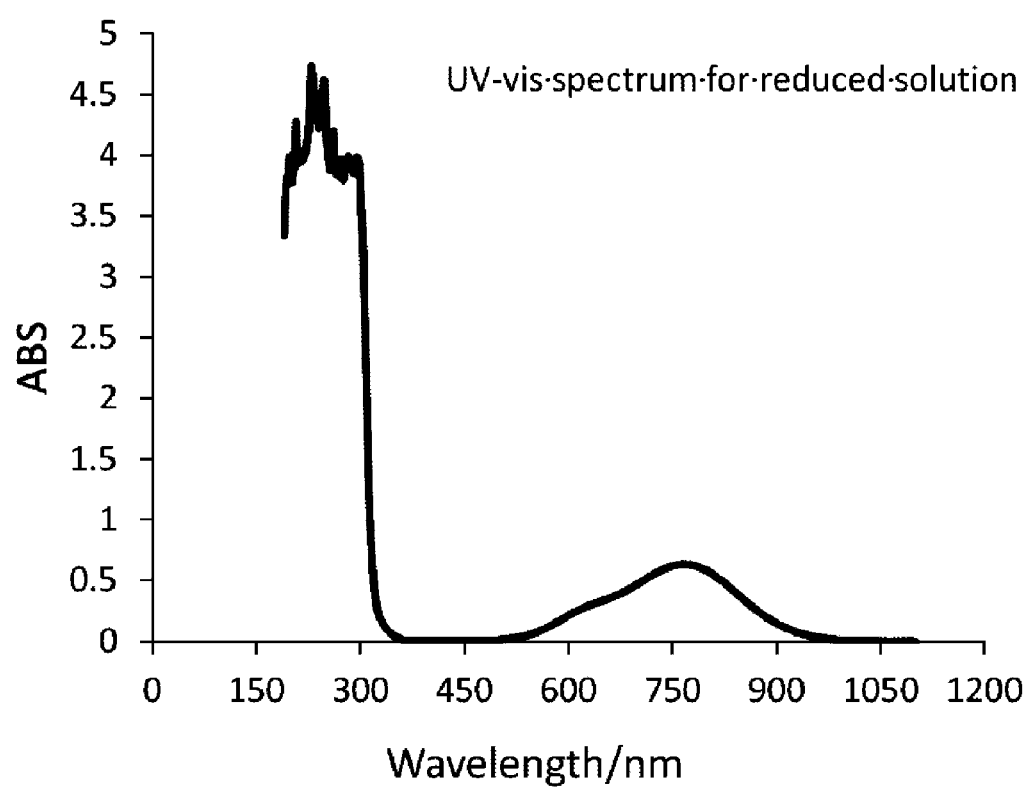
FIG. 3 is an optical absorbance spectrum of a $VO_2^+$ solution that has been fully reduced to $VO^{2+}$ in accordance with an embodiment of the present disclosure.

Excess sodium sulfite solution (0.5 mol/L) is added to a $VO_2^+/VO^{2+}$ solution ($C_{vanadium}=0.03$ mol/L) to reduce $VO_2^+$ ions to $VO^{2+}$ ions. The following reaction takes place: $2VO_2^+ + SO_3^{2-} + 2H^+ \rightarrow 2 VO^{2+} + SO_4^{2-} + H_2O$. Referring to FIG. 3, an absence of absorption at wavelength of around 400 nm in the reduced solution showed that $VO_2^+$ ions were completely reduced to $VO^{2+}$ ions and that no $V^{3+}$ ions formed during the reducing process.

Example 2

Absorbance Vs. $VO^{2+}$ Concentration in $VO^{2+}/VO_2^+$ Solution

Figure 4:
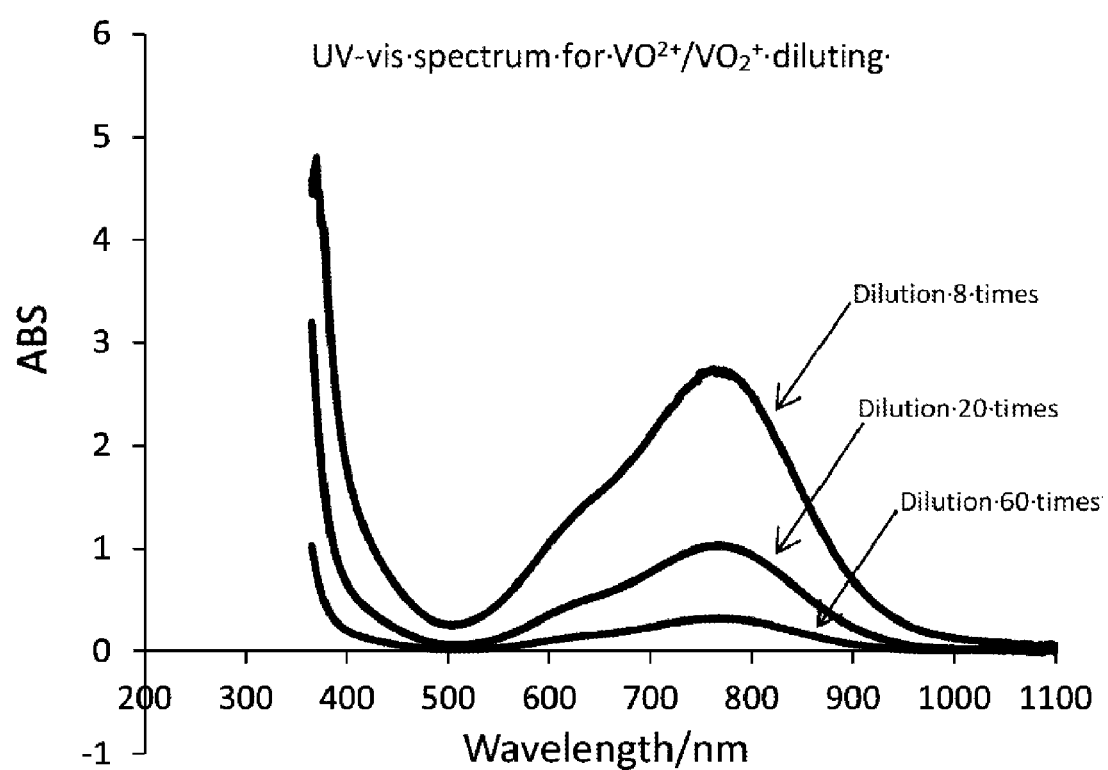
FIG. 4 is an optical absorbance spectrum of serially diluted solutions of $VO^{2+}$ and $VO_2^+$ in accordance with an embodiment of the present disclosure.
Figure 5:
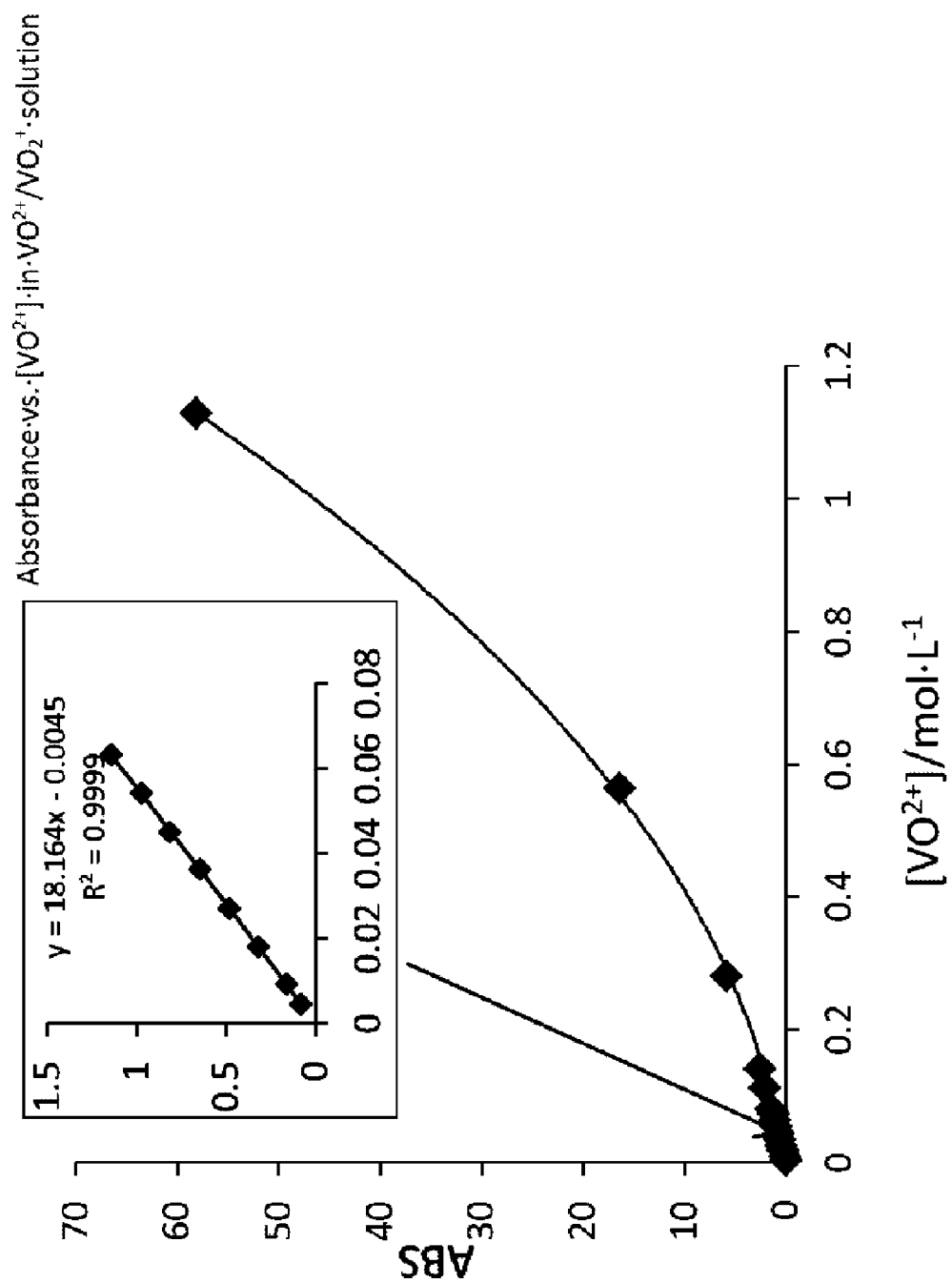
FIG. 5 is a graph showing absorbance vs. concentration for a solution of $VO^{2+}$ and $VO_2^+$ in accordance with an embodiment of the present disclosure.

The concentrations at which $VO^{2+}$ and $VO_2^+$ exist as independent species were investigated. It is believed that $VO^{2+}$ and $VO_2^+$ can form complexes in solution. However, diluting a $VO^{2+}/VO_2^+$ solution could reduce the $VO^{2+}$–$VO_2^+$ complex formation. Referring to FIG. 4, the absorption at wavelength of around 1000-1100 nm, which was attributed to the $VO^{2+}$-$VO_2^+$ complex, disappeared when diluting a $VO^{2+}/VO_2^+$ solution (C=2.26 mol/L) more than 20 times. Referring to FIG. 5, the absorbance versus $VO^{2+}$ concentration in the solution had good linear relationship when diluting more than 20 times. Therefore, the concentration of $VO^{2+}$ in the $VO^{2+}/VO_2^+$ mixed solution could be analyzed using optical absorption spectrophotometry without significant interference when the solution was diluted more than 20 times.

Example 3

Standard Concentration Curve Calibration

A standard concentration calibration curve for $VO^{2+}$ was determined. 1 mL, 3 mL, 6 mL, 10 mL and 12 mL of $VO^{2+}$ standard solutions (0.19585 mol/L) (purchased from Sigma Aldrich, USA) were individually placed in 50 mL volumetric flasks. Then, excess sodium sulfite solution (0.5 mol/L) was added and the mixed solutions were each heated at 40° C. for 3 minutes.

After diluting with deionized water to 50 mL, the solutions were measured by optical absorption spectroscopy at a wavelength of 765 nm.

Figure 6:
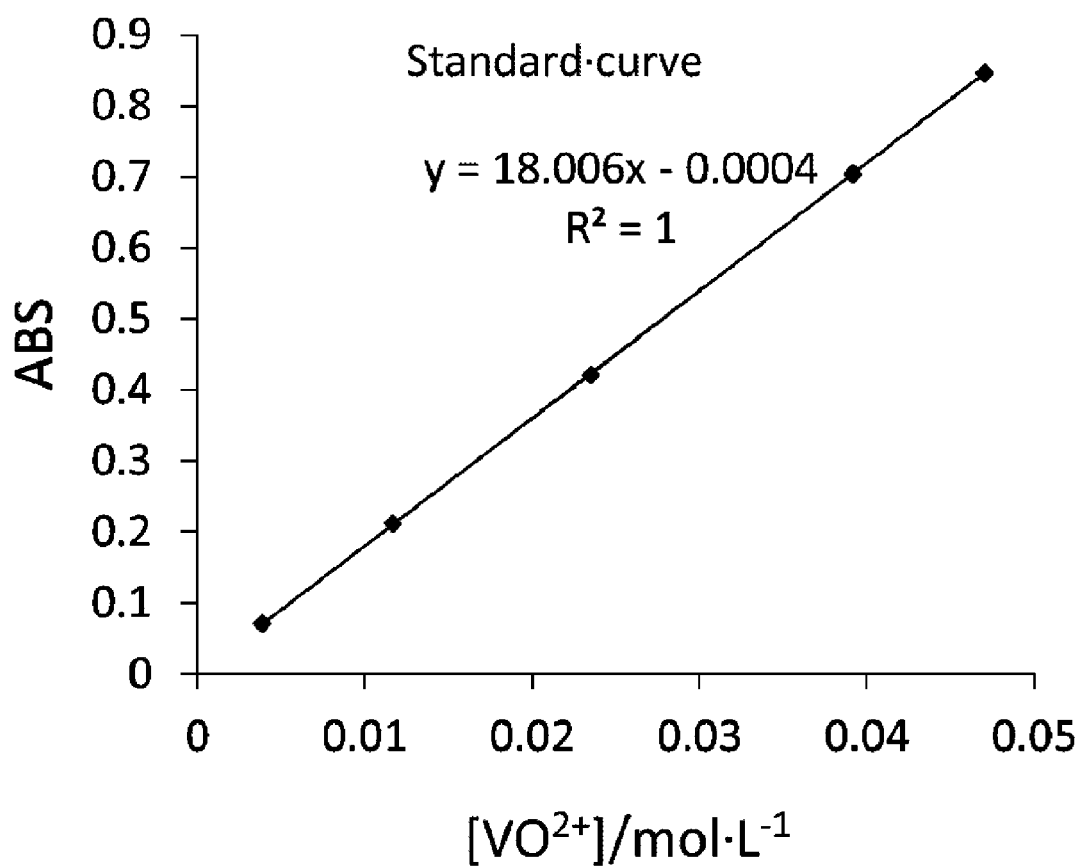
FIG. 6 is a graph showing a standard concentration calibration curve of absorbance vs. concentration for a solution of $VO^{2+}$ and $VO_2^+$ in accordance with an embodiment of the present disclosure.

The standard concentration calibration curve was plotted as shown in FIG. 6. $VO^{2+}$ concentration could be measured according to the standard concentration calibration curve.

Example 4

Vanadium Ion Analysis—General Procedures

Procedures for analysis of vanadium ions at valence states 2+, 3+, 4+ and 5+ are described.

(A) $VO^{2+}$ and $VO_2^+$ Ions:

1.0 mL of $VO^{2+}/VO_2^+$ solution was added into a 100 mL volumetric flask. After diluting with DI water to 100 mL, the solution was analyzed by optical absorption spectroscopy. Referring to FIG. 6, the $VO^{2+}$ concentration ($C_{V(IV)}$) in the sample could be calculated from the standard concentration calibration curve.

The other 100 mL volumetric flask with 1.0 mL of $VO^{2+}/VO_2^+$ solution was prepared, and excess sodium sulfite (0.5 mol/L) was added to reduce $VO_2^+$ to $VO^{2+}$. Then, the mixed solution was heated at 40° C. for 3 minutes. The following reaction takes place:

$$2VO_2^+ + SO_3^{2-} + 2H^+ \rightarrow 2VO^{2+} + SO_4^{2-} + H_2O$$

After diluting with deionized water to 100 mL, the solution was analyzed by optical absorption spectroscopy. Referring again to FIG. 6, the total vanadium concentration ($C_{Vtot}$) can be calculated from the standard concentration calibration curve.

The concentration of $VO_2^+$ ($C_{V(V)}$) in the sample could be calculated by subtracting $VO^{2+}$ concentration from total vanadium concentration ($C_{Vtot}$): $C_{V(V)} = C_{Vtot} - C_{V(IV)}$ (B) $V^{3+}$ and $VO^{2+}$ Ions:

One $VO^{2+}/VO_2^+$ standard solution was prepared. The procedure of vanadium concentration analysis was conducted as discussed in (A). The $VO^{2+}$ and $VO_2^+$ concentrations in the solution were measured as $C_1$ and $C_2$ ($C_2 \geq C_1$, $C_1+C_2=2.0\sim3.0$ mol/L), respectively.

2 mL of $VO^{2+}/VO_2^+$ standard solution was added into a 250 mL volumetric flask. Then, 1 mL of $V^{3+}/VO^{2+}$ solution was added into the flask. The following reaction took place:

$$V^{3+} + VO_2^+ \rightarrow 2VO^{2+}$$

After diluting with deionized water to 250 mL, the solution was measured by optical absorption spectroscopy at the wavelength of 765 nm. Then the $VO^{2+}$ concentration ($C_3$) in this solution was calculated from the standard curve shown in FIG. 6.

The other 250 mL volumetric flask with 2 mL of $VO^{2+}/VO_2^+$ standard solution was prepared, and 1.0 mL of $V^{3+}/VO_2^+$ solution was added. Then, excess sodium sulfite (0.5 mol/L) was added to reduce $VO_2^+$ to $VO^{2+}$, and the mixed solution was heated at 40° C. for 3 minutes. The following reactions took place:

$$V^{3+} + VO_2^+ \rightarrow 2VO^{2+}$$

$$2VO_2^+ + SO_3^{2-} + 2H^+ \rightarrow 2VO^{2+} + SO_4^{2-} + H_2O$$

After diluting with deionized water to 250 mL, the solution was measured by optical absorption spectroscopy at the wavelength of 765 nm. Then the total vanadium concentration ($C_4$) in this solution was calculated from the standard concentration calibration curve shown in FIG. 6.

The $V^{3+}$ concentration in the $V^{3+}/VO^{2+}$ sample could calculated by the following equation: $C_{V(III)} = 2C_2 - 3(C_4 - C_3)$.

The $VO^{2+}$ concentration in the $V^{3+}/VO^{2+}$ sample could be calculated by the following equation: $C_{V(IV)} = 3C_3 - 2C_1 - 2C_{V(III)}$.

(C) $V^{2+}$ and $V^{3+}$ Ions:

One $VO^{2+}/VO_2^+$ standard solution was prepared. The procedure of vanadium concentration analysis was conducted as discussed in (A). The $VO^{2+}$ and $VO_2^+$ concentrations in the solution were measured as $C_1$ and $C_2$ ($C_2 \geq C_1$, $C_1+C_2=2.0\sim3.0$ mol/L), respectively.

3 mL of $VO^{2+}/VO_2^+$ standard solution was added into a 250 mL volumetric flask and purged with argon gas for 2 minutes. Then, 1 mL of $V^{2+}/V^{3+}$ solution was added into the flask and mixed quickly. The following reactions took place:

$$V^{2+} + VO_2^+ + 2H^+ \rightarrow V^{3+} + VO^{2+} + H_2O$$

$$V^{2+} + VO^{2+} + 2H^+ \rightarrow 2V^{3+} + H_2O$$

$$V^{3+} + VO_2^+ \rightarrow 2VO^{2+}$$

After diluting with deionized water to 250 mL, the solution was measured by optical absorption spectroscopy at a wavelength of 765 nm. Then the $VO^{2+}$ concentration ($C_5$) in this solution was calculated from the standard concentration calibration curve shown in FIG. 6.

The other 250 mL volumetric flask with 3 mL of $VO^{2+}/VO_2^+$ standard solution was prepared and purged with argon gas for 2 minutes. Then, 1.0 mL of $V^{2+}/V^{3+}$ solution was added and mixed quickly. After that, excess sodium sulfite (0.5 mol/L) was added to reduce $VO_2^+$ to $VO^{2+}$, and the mixed solution was heated at 40° C. for 3 minutes. The following reactions take place:

$$V^{2+} + VO_2^+ + 2H^+ \rightarrow V^{3+} + VO^{2+} + H_2O$$

$$V^{2+} + VO^{2+} + 2H^+ \rightarrow 2V^{3+} + H_2O$$

$$V^{3+} + VO_2^+ \rightarrow 2VO^{2+}$$

$$2VO_2^+ + SO_3^{2-} + 2H^+ \rightarrow 2VO^{2+} + SO_4^{2-} + H_2O$$

After diluting with deionized water to 250 mL, the solution was measured by optical absorption spectroscopy at 765 nm. Then the total vanadium concentration ($C_6$) in this solution was calculated from the standard concentration calibration curve shown in FIG. 6.

The $V^{2+}$ concentration in the $V^{2+}/V^{3+}$ sample could be calculated by the following equation:

$$C_{V(II)}=3(C_1+2C_2)-4(2C_6-C_5).$$

The $V^{3+}$ concentration in the $V^{2+}/V^{3+}$ sample could be calculated by the following equation:

$$C_{V(III)}=3C_2-4(C_6-C_5)-2C_{V(II)}.$$

Example 5

Determination of $V^{4+}$ and $V^{5+}$ Concentrations

The concentrations of vanadium ions at valence states 4+ and 5+ were determined in a $V^{4+}/V^{5+}$ electrolyte solution.

1.0 mL of $VO^{2+}/VO_2^+$ solution (Sample 1) was added into a 100 mL volumetric flask. After diluting with deionized water to 100 mL, the solution was measured by optical absorption spectroscopy at the wavelength of 765 nm. The absorbance of the solution was measured as $A^u{}_{765nm}=0.262$. Then the $VO^{2+}$ concentration ($C_{V(IV)}$) in Sample 1 was calculated by standard concentration calibration curve, shown in FIG. 6: $C_{V(IV)}=((0.262+0.0004)/18.006)\times 100=1.457$ (mol/L).

The other 100 mL volumetric flask with 1.0 mL of $VO^{2+}/VO_2^+$ solution (Sample 1) was prepared, and excess sodium sulfite (0.5 mol/L) was added to reduce $VO_2^+$ to $VO^{2+}$. Then, the mixed solution was heated at 40° C. for 3 minutes. The following reaction takes place:

$$2VO_2^+ + SO_3^{2-} + 2H^+ \rightarrow 2VO^{2+} + SO_4^{2-} + H_2O$$

After diluting with deionized water to 100 mL, the solution was measured by optical absorption spectroscopy at the wavelength of 765 nm. The absorbance of the solution is measured as $A^u{}_{765nm}=0.303$. Then, the total vanadium concentration in Sample 1 was calculated ($C_{Vtot}$) from the standard concentration calibration curve shown in FIG. 6: $C_{Vtot}=((0.303+0.0004)/18.006)\times 100=1.685$ (mol/L).

The concentration of $VO_2^+$ ($C_{V(V)}$) in Sample 1 was calculated by subtracting $VO^{2+}$ concentration from total vanadium concentration: $C_{V(V)}=C_{Vtot}-C_{V(IV)}=1.685-1.457=0.228$ (mol/L)

tions in the solution were measured as $C_1=1.064$ mol/L and $C_2=1.106$ mol/L, respectively.

2 mL of $VO^{2+}/VO_2^+$ standard solution was added into a 250 mL volumetric flask. Then, 1 mL of $V^{3+}/VO^{2+}$ solution (Sample 2) was added into the flask. The following reaction takes place:

$$V^{3+} + VO_2^+ \rightarrow 2VO^{2+}$$

After diluting with deionized water to 250 mL, the solution was measured by optical absorption spectroscopy at 765 nm. The absorbance of this solution was measured as $A^u{}_{765nm}=0.390$. Then the $VO^{2+}$ concentration ($C_3$) in this solution was calculated from the standard concentration calibration curve as shown in FIG. 6: $C_3=((0.390+0.0004)/18.006)\times 250/3=1.807$ (mol/L).

The other 250 mL volumetric flask with 2 mL of $VO^{2+}/VO_2^+$ standard solution was prepared, and 1.0 mL of $V^{3+}/VO^{2+}$ solution (Sample 2) was added. Then, excess sodium sulfite (0.5 mol/L) was added to reduce $VO_2^+$ to $VO^{2+}$, and the mixed solution was heated at 40° C. for 3 minutes. The following reactions take place:

$$V^{3+} + VO_2^+ \rightarrow 2VO^{2+}$$

$$2VO_2^+ + SO_3^{2-} + 2H^+ \rightarrow 2VO^{2+} + SO_4^{2-} + H_2O$$

After diluting with deionized water to 250 mL, the solution was measured by optical absorption spectroscopy at 765 nm. The absorbance of this solution was measured as $A^u{}_{765nm}=0.472$. Then the total vanadium concentration ($C_4$) in this solution was calculated from the standard concentration calibration curve as shown in FIG. 6: $C_4=((0.472+0.0004)/18.006)\times 250/3=2.186$ (mol/L).

The $V^{3+}$ concentration in Sample 2 can be calculated by the following equation.

$$C_{V(III)}=2C_2-3(C_4-C_3)=2\times 1.106-3\times(2.186-1.807)=1.075 \text{ (mol/L)}$$

The $VO^{2+}$ concentration in Sample 2 can be calculated by the following equation.

$$C_{V(IV)}=3C_3-2C_1-2C_{V(III)}=3\times 1.807-2\times 1.064-2\times 1.075=1.143 \text{ (mol/L)}$$

TABLE 1

Comparison of concentrations of vanadium ions in Sample 1 using different analysis methods

| Method | Sample 1 | | |
|---|---|---|---|
| | $VO^{2+}$ | $VO_2^+$ | $V_{tot}$ |
| Optical Absorption Spectroscopy | 1.457 | 0.228 | 1.685 |
| Potentiometric Titration | 1.419 | 0.233 | 1.652 |
| Inductively Coupled Plasma | — | — | 1.670 |
| Relative Error (%) (Optical absorption spectroscopy compared with potentiometric titration) | 2.68 | 2.15 | 2.00 |

TABLE 2

Comparison of the measurements of Sample 2 using different analysis methods

| Method | Sample 2 | | |
|---|---|---|---|
| | $V^{3+}$ | $VO^{2+}$ | $V_{tot}$ |
| Optical Absorption Spectroscopy | 1.075 | 1.143 | 2.218 |
| Potentiometric Titration | 1.10 | 1.15 | 2.25 |
| Inductively Coupled Plasma | — | — | 2.102 |
| Relative Error (%) (optical absorption spectroscopy compared with potentiometric titration) | 2.27 | 0.61 | 1.42 |

Example 6

Determination of $V^{3+}$ and $V^{4+}$ Concentrations

The concentrations of vanadium ions at valence states 3+ and 4+ were determined in a $V^{3+}/V^{4+}$ electrolyte solution.

One $VO^{2+}/VO_2^+$ standard solution was prepared. The procedure of vanadium concentration analysis was conducted as the Example 4A. The $VO^{2+}$ and $VO_2^+$ concentra-

Example 7

Determination of $V^{2+}$ and $V^{3+}$ Concentrations

The concentrations of vanadium ions at valence states 2+ and 3+ were determined in a $V^{2+}/V^{3+}$ electrolyte solution.

One $VO^{2+}/VO_2^+$ standard solution was prepared. The procedure of vanadium concentration analysis was conducted as in Example 4(A). The $VO^{2+}$ and $VO_2^+$ concentrations in the solution were measured as $C_1=1.064$ mol/L and $C_2=1.106$ mol/L, respectively.

3 mL of $VO^{2+}/VO_2^+$ standard solution was added into a 250 mL volumetric flask and purged with argon gas for 2 minutes. Then, 1 mL of $V^{2+}/V^{3+}$ solution (Sample 3) was added into the flask and mixed quickly. The following reactions take place:

$$V^{2+}+VO_2^++2H^+\rightarrow V^{3+}+VO^{2+}+H_2O$$

$$V^{2+}+VO^{2+}+2H^+\rightarrow 2V^{3+}+H_2O$$

$$V^{3+}+VO_2^+\rightarrow 2VO^{2+}$$

After diluting with deionized water to 250 mL, the solution was measured by optical absorption spectroscopy at 765 nm. The absorbance of this solution was measured as $A^u_{765nm}=0.547$. Then the $VO^{2+}$ concentration ($C_5$) in this solution can be calculated by standard concentration calibration curve (FIG. 5): $C_5=((0.547+0.0004)/18.006)\times 250/4=1.900$ (mol/L).

The other 250 mL volumetric flask with 3 mL of $VO^{2+}/VO_2^+$ standard solution was prepared and purged with argon gas for 2 minutes. Then, 1.0 mL of $V^{2+}/V^{3+}$ solution (Sample 3) was added and mixed quickly. After that, excess sodium sulfite (0.5 mol/L) was added to reduce $VO_2^+$ to $VO^{2+}$, and the mixed solution was heated at 40° C. for 3 minutes. The following reactions take place:

$$V^{2+}+VO_2^++2H^+\rightarrow V^{3+}+VO^{2+}+H_2O$$

$$V^{2+}+VO^{2+}+2H^+\rightarrow 2V^{3+}+H_2O$$

$$V^{3+}+VO_2^+\rightarrow 2VO^{2+}$$

$$2VO_2^++SO_3^{2-}+2H^+\rightarrow 2VO^{2+}+SO_4^{2-}+H_2O$$

After diluting with deionized water to 250 mL, the solution was measured by optical absorption spectroscopy at 765 nm. The absorbance of this solution was measured as $A^u_{765nm}=0.585$. Then the total vanadium concentration ($C_6$) in this solution was calculated from the standard concentration calibration curve as shown in FIG. 6: $C_6=((0.585+0.0004)/18.006)\times 250/4=2.032$ (mol/L).

The $V^{2+}$ concentration in the Sample 3 was calculated by the following equation.

$$C_{V(II)}=3(C_1+2C_2)-4(2C_6-C_5)=3\times(1.064+2\times1.106)-4\times(2\times2.032-1.900)=1.172 \text{ (mol/L)}$$

The $V^{3+}$ concentration in Sample 3 can be calculated by the following equation.

$$C_{V(III)}=3C_2-4(C_6-C_5)-2C_{V(II)}=3\times1.106-4\times(2.032-1.900)-2\times1.172=0.446 \text{ (mol/L)}$$

TABLE 3

Comparison of the measurements of Sample 3 using different analysis methods

| Method | Sample 3 | | |
|---|---|---|---|
| | $V^{2+}$ | $V^{3+}$ | $V_{tot}$ |
| Optical Absorption Spectroscopy | 1.172 | 0.446 | 1.618 |
| Potentiometric Titration | 1.165 | 0.457 | 1.622 |
| Inductively Coupled Plasma | — | — | 1.602 |
| Relative Error (%) (optical absorption spectroscopy compared with potentiometric titration) | 0.60 | 2.41 | 0.25 |

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

While illustrative embodiments have been illustrated and described, it will be appreciated that various changes can be made therein without departing from the spirit and scope of the disclosure.

What is claimed is:

1. A method of determining a vanadium ion concentration in a vanadium redox flow battery, comprising:
   step (a), or a combination of steps (b) and (c), wherein
   step (a): providing an electrolyte solution comprising $V^{3+}$ and $V^{4+}$; converting the $V^{3+}$ to $V^{4+}$; determining a concentration of each of $V^{3+}$ and $V^{4+}$ in the electrolyte solution, and determining an amount of $V^{3+}$ and $V^{4+}$ based on the concentration of each of $V^{3+}$ and $V^{4+}$ and a volume of the electrolyte solution;
   step (b): providing a catholyte solution comprising $V^{4+}$ and $V^{5+}$, converting the $V^{5+}$ to $V^{4+}$; determining a concentration of each of $V^{5+}$ and $V^{4+}$ in the catholyte solution, and determining an amount of $V^{4+}$ and $V^{5+}$ based on the concentration of each of $V^{4+}$ and $V^{5+}$ and a volume of the catholyte solution; and
   step (c): providing an anolyte solution comprising $V^{2+}$, $V^{3+}$, or both $V^{2+}$ and $V^{3+}$; converting each of the $V^{2+}$ and $V^{3+}$, when present, to $V^{4+}$ by exposing each of the $V^{2+}$ and $V^{3+}$ to a first solution containing known concentrations of $V^{5+}$ and $V^{4+}$; determining a concentration of each of $V^{2+}$ and $V^{3+}$, when present in the anolyte solution; and determining an amount of $V^{2+}$, $V^{3+}$, or both $V^{2+}$ and $V^{3+}$ based on the concentration of each of $V^{2+}$, $V^{3+}$, when present, and a volume of the anolyte solution.

2. The method of claim 1, wherein in step (a), converting the $V^{3+}$ to $V^{4+}$ comprises exposing the $V^{3+}$ to an oxidizing agent comprising a second solution containing known concentrations of $V^{5+}$ and $V^{4+}$.

3. The method of claim 1, wherein in step (a) further comprises using optical absorption spectroscopy to determine the concentration of each of $V^{3+}$ and $V^{4+}$ in the electrolyte solution.

4. The method of claim 1, wherein in step (b), converting the $V^{5+}$ to $V^{4+}$ comprises exposing the $V^{5+}$ to a reducing agent selected from the group consisting of $Sn^{2+}$, $Fe^{2+}$, sulfites, phosphites, hypophosphites, phosphorous acid, metal hydrides, metals, metal amalgams, and diboranes.

5. The method of claim 1, wherein in step (b), converting the $V^{5+}$ to $V^{4+}$ comprises exposing the $V^{5+}$ to a sulfite.

6. The method of claim 1, wherein in step (b), converting the $V^{5+}$ to $V^{4+}$ comprises exposing the $V^{5+}$ to a reducing agent selected from the group consisting of sugars, alcohols, organic acids, oils, and hydrocarbons.

7. The method of claim 1, wherein step (b) further comprises using optical absorption spectroscopy to determine the concentration of each of $V^{5+}$ and $V^{4+}$ in the catholyte solution and step (c) further comprises using optical absorption spectroscopy to determine the concentration of each of $V^{2+}$ and $V^{3+}$, when present, in the anolyte solution.

\* \* \* \* \*